United States Patent [19]

Leconte et al.

[11] Patent Number: 5,908,803
[45] Date of Patent: Jun. 1, 1999

[54] PROCESS FOR ISOLATION OF A CATALYST CONTAINING PALLADIUM

[75] Inventors: Philippe Leconte, Meyzieu; Carl Patois, Lyons, both of France

[73] Assignee: Rhone-Poulenc Fiber & Resin Intermediates, Courbevoie Cedex, France

[21] Appl. No.: 08/831,580

[22] Filed: Apr. 9, 1997

Related U.S. Application Data

[63] Continuation of application No. PCT/FR96/01130, Jul. 18, 1996
[60] Provisional application No. 60/015,478, Apr. 12, 1996.

[30] Foreign Application Priority Data

Aug. 9, 1995 [FR] France .................................. 95 09807

[51] Int. Cl.⁶ ........................... B01J 20/34; C07C 51/14; C07C 57/02
[52] U.S. Cl. .............................. 502/27; 502/22; 562/522; 562/598
[58] Field of Search ........................ 502/22, 27; 562/522, 562/598

[56] References Cited

U.S. PATENT DOCUMENTS

| | | | |
|---|---|---|---|
| 3,857,895 | 12/1974 | Booth | 260/604 |
| 3,928,231 | 12/1975 | Frankel | 252/413 |
| 5,288,903 | 2/1994 | Bunel et al. | 562/598 |
| 5,625,096 | 4/1997 | Denis et al. | 562/522 |

FOREIGN PATENT DOCUMENTS

| | | |
|---|---|---|
| 0 337 803 A1 | 10/1989 | European Pat. Off. . |
| 0 546 324 A1 | 6/1993 | European Pat. Off. . |
| 0 552 846 A1 | 7/1993 | European Pat. Off. . |

*Primary Examiner*—Steven Bos
*Assistant Examiner*—Alexander G. Ghyka
*Attorney, Agent, or Firm*—Burns, Doane, Swecker & Mathis, L.L.P.

[57] ABSTRACT

The present invention relates to the isolation of a palladium-based catalyst from a mixture in which it is dissolved. More specifically, the invention relates to the isolation of a palladium-based catalyst from a mixture originating from the reaction of hydroxycarbonylation of butadiene to pentenoic acids. It therefore consists of a process for the isolation of at least a portion of the palladium dissolved in a solution also containing at least 3-pentenoic acid, characterized in that the said solution is acidified and stirred with an aqueous solution of hydrochloric acid, so as to obtain two liquid phases including an aqueous phase containing at least a portion of the palladium.

33 Claims, No Drawings

PROCESS FOR ISOLATION OF A CATALYST CONTAINING PALLADIUM

CROSS-REFERENCE TO RELATED APPLICATIONS

This application is a continuation of International Patent Application No. PCT/FR96/01130, filed Jul. 18, 1996 and designating the United States, and also claims the priority of U.S. Provisional Application No. 60/015,478, filed Apr. 12, 1996.

BACKGROUND OF THE INVENTION

1. Technical Field of the Invention

The present invention relates to the isolation of a palladium-based catalyst from a mixture in which it is dissolved.

2. Description of the Prior Art

More specifically, the invention relates to the isolation of a palladium-based catalyst from a mixture originating from the reaction of hydroxycarbonylation of butadiene to pentenoic acids.

One of the objectives of the process of the invention lies in the isolation of at least a portion of the catalyst containing palladium which is dissolved in the form of organometallic complex in the mixture to be treated, in order to enable this catalyst containing palladium to be recycled into a new butadiene hydroxycarbonylation reaction.

A second objective of the process is to make it possible to isolate at least a portion of the pentenoic acids present in the said mixture.

The hydroxycarbonylation of butadiene and/or of its derivatives, such as especially the allylbutenols like 3-buten-2-ol, 2-buten-1-ol and their mixtures, the compounds of addition of hydrogen chloride to butadiene (chlorobutenes), the main one of which is crotyl chloride, can be performed using water and carbon monoxide at a pressure that is higher than atmospheric pressure and in the presence of a catalyst containing palladium, soluble in the reaction mixture.

Reference may be made, for example, to Patent EP A 0 648 731 for a more detailed description of such a technique, although the present invention is not limited to the treatment of reaction mixtures originating from the process according to this patent.

The reaction mixtures used in the process of the invention contain more or less considerable quantities of the compounds involved in the hydroxycarbonylation reaction and of the compounds formed during this reaction.

Apart from the palladium catalyst, which may be present in various chemical forms, the reaction mixture contains the pentenoic acids formed, especially 3-pentenoic acid, water, hydrochloric acid, in most cases also reaction by-products like butenes or valeric acid, dicarboxylic acids like adipic acid, 2-methylglutaric acid and 2-ethylsuccinic acid, optionally butadiene which has not been converted and any optional solvent used in the reaction.

The invention consists therefore of a process for isolation of at least a portion of the palladium dissolved in a solution also containing at least 3-pentenoic acid, characterized in that the said solution is acidified and stirred with an aqueous solution of hydrochloric acid, so as to obtain two liquid phases, including an aqueous phase containing at least a portion of the palladium.

When the solution to be treated originates directly from a butadiene hydroxycarbonylation operation, it is obviously necessary to eliminate the carbon monoxide pressure before the acidification.

The aqueous solution of hydrochloric acid employed generally contains from 5% to 40% by weight of hydrochloric acid by weight of solution.

In general the solution of hydrochloric acid is added in a proportion of 0.1 to 2 times the volume of the solution to be treated.

The formation of two liquid phases during the acidification may originate simply from the addition of the aqueous solution of hydrochloric acid according to the composition of the solution to be treated.

This is particularly, but not exclusively, the case when the solution to be treated contains an essentially water-immiscible solvent such as an aromatic, aliphatic or cycloaliphatic hydrocarbon or a chlorinated aromatic, chlorinated aliphatic or chlorinated cycloaliphatic hydrocarbon.

Separation into two liquid phases may also be obtained by the addition of a water-immiscible organic solvent. This addition may be performed after the acidification, at the time of the acidification or, if appropriate, before the acidification.

The presence of a water-immiscible organic solvent makes it possible to extract at least a portion of the pentenoic acids present in the solution to be treated.

The temperature at which the solution to be treated is acidified is not really critical for making use of the process. It is thus possible to operate between 0° C. and 230° C. (temperature at which the previous hydroxycarbonylation reaction may be conducted). In practice, however, the operation will take place between 20° C. and 200° C. and preferably between 40° C. and 110° C.

The acidification with hydrochloric acid allows the palladium present in the form of organometallic complex in the solution to be treated to be converted into palladium dihydrotetrachloride. The temperature at which the operation is performed affects the rate of this conversion of the palladium compounds, a higher temperature accelerating this conversion, but running the risk of precipitating a proportion of the palladium.

The organic solvent employed for performing the extraction is chosen advantageously from aromatic, aliphatic or cycloaliphatic hydrocarbons and chlorinated aromatic, chlorinated aliphatic or chlorinated cycloaliphatic hydrocarbons which are liquid in the operating conditions and are essentially immiscible with water.

For convenience, the boiling point of the organic solvent will be lower than that of 3-pentenoic acid.

Nonlimiting examples of these solvents which may be mentioned are benzene, toluene, xylenes, chlorobenzenes, cyclohexane, butadiene, butenes, alkanes such as hexanes, heptanes, octanes, nonanes, decanes, undecanes, dodecanes, and the various mixtures of several of these solvents.

The mixture obtained after acidification of the solution to be treated and, if appropriate, after addition of the organic solvent and stirring, separates at rest into an organic phase and an aqueous phase.

As in the case of the acidification, the extraction with the organic solvent may be performed at a temperature situated between 0° C. and 230° C., more often between 20° C. and 200° C. and preferably between 40° C. and 110° C.

The organic phase contains more than half of the initial quantity of pentenoic acids, most of the butadiene and of the butenes and a portion of the dicarboxylic acids which may be present in the solution to be treated.

The aqueous phase contains more than half of the quantity of palladium as well as a portion of the dicarboxylic acids which may be present in the solution to be treated.

The operation of extraction with the aid of an organic solvent may be repeated a number of times if desired.

Depending on the organic solvent employed, the quantity of pentenoic acids in the organic phase may exceed 60% and even 75% of the quantity initially present in the solution to be treated. The pentenoic acids, and more particularly 3-pentenoic acid, may next be isolated from the organic phase by the usual means of chemistry.

The aqueous phase generally contains more than 60% and preferably more than 80% of the palladium initially present in the solution to be treated. With the process of the invention it is even possible to recover in the aqueous phase up to virtually all of the palladium.

The aqueous phase containing the palladium may advantageously be recycled into a new butadiene hydroxycarbonylation reaction. It is generally desirable to distill off beforehand a proportion of the hydrochloric acid which it contains so as to adjust the quantity of hydrochloric acid to the quantity which it is convenient to have for the hydroxycarbonylation. A solution of hydrochloric acid corresponding to the water/hydrogen chloride azeotrope is obtained by such a distillation. In the context of a continuous industrial process it is particularly advantageous to employ the hydrochloric acid solution thus obtained for acidifying the initial solution to be treated, after addition of the top-up which may be necessary.

An alternative form of the process of the invention consists in distilling off at least a portion of the pentenoic acids from the solution to be treated before carrying out the acidification.

Such a distillation will be performed at a temperature lower than or equal to 110° C. This temperature restriction is important because it has been observed that, if the operation is carried out at a higher temperature, a portion of the palladium precipitates. Even when partial, such a precipitation is unacceptable in an industrial process. In effect, it gives rise to losses of a very costly metal and in addition it seriously complicates the treatment of the reaction mixtures.

Unexpectedly, if the operation is carried out at a temperature which is lower than or equal to 110° C., and still more preferably at a temperature which is lower than or equal to 105° C., no precipitation of palladium is observed.

In order to be able to conform to this upper temperature limit, it sometimes suffices to operate at atmospheric pressure. More often, it is necessary to distill the pentenoic acids at a pressure that is lower than atmospheric pressure, generally of the order of 2 kPa to 7 kPa.

The lighter compounds which may be present in the solution to be treated also distill off with the pentenoic acids, like, to give examples, butadiene, butenes, water, possibly a portion of the dicarboxylic acids and the solvent which may be present.

The residue obtained after this distillation contains the palladium and the heavier compounds, like another portion of the dicarboxylic acids. This residue is next treated as described above, with the aid of an aqueous solution of hydrochloric acid generally containing from 5% to 40% by weight of hydrochloric acid by weight of solution. It is not essential to perform the extraction with the aid of an organic solvent as in the first alternative form which has been described.

As already stated, the temperature at which the solution to be treated is acidified may lie between 0° C. and 230° C., in practice between 20° C. and 200° C. and preferably between 40° C. and 110° C.

The acidified aqueous solution containing the palladium may be recycled into a new butadiene hydroxycarbonylation reaction as previously, if appropriate after distillation of the excess hydrochloric acid.

In an equivalent quantity, recycled palladium exhibits a catalytic activity similar to that observed with a new catalyst.

Besides the recycling, in a homogeneous form, of the catalyst containing palladium and the isolation of at least a portion of the pentenoic acids formed, the process of the invention permits the removal of a portion of the by-products of the butadiene hydroxycarbonylation reaction, especially of the dicarboxylic acids, the accumulation of which can prove to be detrimental for the said butadiene hydroxycarbonylation reaction.

The examples which follow illustrate the invention.

EXAMPLES 1 TO 3

The following are placed successively in a magnetically stirred round bottom flask:

67 mg of $PdCl_2$ 360 mg of 37% HCl 8 g of 3-pentenoic acid (P3)

9 g of 2-methylglutaric acid 3 g of 2-ethylsuccinic acid 20 ml of HCl at a concentration of 10% by weight in water and 20 ml of an organic solvent (shown in Table 1 below) are added next. The mixture is left stirred at ambient temperature for 30 minutes. The two phases are separated by settling and the palladium in these two phases is determined. In all cases no precipitate is observed. The results of the determinations are brought together in Table 1.

TABLE 1

| Examples | Organic solvent | Pd: % in the aqueous phase | Pd: % in the organic phase |
| --- | --- | --- | --- |
| Example 1 | toluene | 100 | 0 |
| Example 2 | cyclohexane | 84 | 16 |
| Example 3 | dodecane | 80 | 20 |

EXAMPLES 4 TO 7

The following are placed successively in a magnetically stirred round bottom flask:

66.8 mg of $\pi$-crotyl-Pd-Cl 242 mg of chlorobutene 8.02 g of 3-pentenoic acid (P3)

9.04 g of 2-methylglutaric acid 3 g of 2-ethylsuccinic acid.

The whole is heated to 50° C. to obtain a homogeneous solution and then returned to a temperature T° C.

20 g of a solution of HCl in water (HCl concentration C% shown in Table 2) and 20 g of toluene are then added.

At the end of stirring for a period which can vary according to the examples, the two phases are separated by settling. Palladium and the organic products are determined in both phases.

The partition coefficients of the various products are the following (ratios of the aqueous layer/organic layer mass fractions) and are brought together in Table 2 below.

TABLE 2

| Examples | HCl C % by weight | T °C. | stirring period | Pd | P3 | diacids |
|---|---|---|---|---|---|---|
| Example 4 | 10 | 40 | 90 min | >1300 | 0.22 | 1.7 |
| Example 5 | 10 | 70 | 90 min | 440 | 0.28 | 2.0 |
| Example 6 | 20 | 40 | 60 min | 350 | 0.13 | 0.9 |
| Example 7 | 37 | 45 | 60 min | 700 | 0.16 | 0.9 |

EXAMPLE 8

Example 6 is repeated, 83 mmol of butadiene being additionally passed through the mixture by bubbling during the extraction.

The following partition coefficients are obtained:

Pd=36
P3=0.13
diacids=0.9

EXAMPLE 9

The following are charged successively into a 250 ml round bottom flask:

1.668 g (9.4 mmol, that is 1 g of Pd) of $PdCl_2$ 54.08 g of HCl at a concentration of 37% by weight in water 4.07 g of 3-pentenoic acid $H_2O$, quantity sufficient for 100 g of solution.

Distillation is carried out at atmospheric pressure until approximately 70 ml of distillate (74.15 g) are obtained. This distillate contains 3.2 g of β-pentenoic acid. The vapor is at a temperature of 106–107° C. and the temperature in the round bottom flask does not exceed 100° C. No palladium precipitation is found at all.

EXAMPLE 10

A 100 ml single-neck round bottom flask is charged with a reaction mixture originating from a butadiene hydroxycarbonylation reaction in the presence of π-crotylpalladium chloride. This mixture has the following composition:

0.0707 g (0.357 mmol) of π-crotylpalladium chloride 0.2706 of chlorobutene (or crotyl chloride)

8.0 g of 3-pentenoic acid 9.1 g of 2-methylglutaric acid 3.11 g of 2-ethylsuccinic acid.

To this reaction mixture are added:

21 g of dichloroethane 21 g of an aqueous solution of hydrochloric acid at a concentration of 20% by weight.

The round bottom flask, with a condenser fitted on top, is placed in an oil bath.

The mixture is kept stirred at 40° C. for 1 h.

After stopping the stirring and separation by density, samples are taken from both of the liquid phases obtained, to determine the palladium.

Practically all the palladium present in the starting mixture is found again.

The aqueous phase/organic phase mass partition coefficient is 32.

What is claimed is:

1. A process for isolating at least a portion of the palladium dissolved in a solution also comprising at least 3-pentenoic acid, said process comprising acidifying and stirring said solution with an aqueous solution of hydrochloric acid to afford two liquid phases, one of said phases being an aqueous phase comprising at least a portion of the palladium.

2. A process according to claim 1, wherein the aqueous solution of hydrochloric acid employed comprises from 5% to 40% by weight of hydrochloric acid by weight of solution.

3. A process according to claim 1, wherein the aqueous solution of hydrochloric acid is added in a proportion of 0.2 to 2 times the volume of the solution to be treated.

4. A process according to claim 2, wherein the aqueous solution of hydrochloric acid is added in a proportion of 0.2 to 2 times the volume of the solution to be treated.

5. A process according to claim 1, wherein the two liquid phases are formed simply by adding the aqueous solution of hydrochloric acid.

6. A process according to claim 1 wherein the two liquid phases are formed simply by adding the aqueous solution of hydrochloric acid.

7. A process according to claim 3, wherein the two liquid phases are formed simply by adding the aqueous solution of hydrochloric acid.

8. A process according to claim 5, wherein the solution to be treated further comprises an essentially water-immiscible solvent.

9. A process according to claim 5, wherein the solution to be treated further comprises an essentially water-immiscible solvent.

10. A process according to claim 7, wherein the solution to be treated further comprises an essentially water-immiscible solvent.

11. A process according to claim 8, wherein the essentially water-immiscible solvent is an aromatic, aliphatic or cycloaliphatic hydrocarbon or a chlorinated aromatic, chlorinated aliphatic or chlorinated cycloaliphatic hydrocarbon.

12. A process according to claim 9, wherein the essentially water-immiscible solvent is an aromatic, aliphatic or cycloaliphatic hydrocarbon or a chlorinated aromatic, chlorinated aliphatic or chlorinated cycloaliphatic hydrocarbon.

13. A process according to claim 10, wherein the essentially water-immiscible solvent is an aromatic, aliphatic or cycloaliphatic hydrocarbon or a chlorinated aromatic, chlorinated aliphatic or chlorinated cycloaliphatic hydrocarbon.

14. A process according to claim 1, wherein the two liquid phases are formed by adding an essentially water-immiscible organic solvent after acidification, at the time of acidification or before acidification.

15. A process according to claim 14, wherein the essentially water-immiscible organic solvent is an aromatic, aliphatic or cycloaliphatic hydrocarbon or a chlorinated aromatic, chlorinated aliphatic or chlorinated cycloaliphatic hydrocarbon which is liquid under the operating conditions employed.

16. A process according to claim 15, wherein the essentially water-immiscible organic solvent is benzene, toluene, a xylene, a chlorobenzene, cyclohexane, butadiene, a butene, an alkane or a mixture of several of these solvents.

17. A process according to claim 16, wherein the alkane is a hexane, a heptane, an octane, a nonane, a decane, an undecane or a dodecane.

18. A process according claim 1, wherein a palladium-based catalyst is isolated from a mixture originating from hydroxycarbonylation of butadiene to pentenoic acids.

19. A process according to claim 1, wherein the two phases obtained are separated by density separation to afford an organic phase which comprises more than half of the initial quantity of pentenoic acids, most of the butadiene and butenes, and a portion of the dicarboxylic acids which may be present in the solution to be treated, and an aqueous phase which comprises more than half of the quantity of palladium, and a portion of the dicarboxylic acids which may be present in the solution to be treated.

20. A process according to claim 18, wherein the aqueous phase comprising the palladium is recycled into a new butadiene hydroxycarbonylation.

21. A process according to claim 20, wherein a portion of the hydrochloric acid present is removed by distillation to adjust the quantity of hydrochloric acid to a quantity suitable for the new hydroxycarbonylation.

22. A process according to claim 21, wherein the hydrochloric acid solution removed is a water/hydrogen chloride azeotrope which is employed for acidifying the initial solution to be treated, after addition of the top-up which may be necessary.

23. A process for isolating at least a portion of the palladium dissolved in a solution also comprising at least 3-pentenoic acid, said process comprising removing by distillation at least a portion of the pentenoic acids from said solution and then acidifying said solution with an aqueous solution of hydrochloric acid.

24. A process according to claim 23, wherein the distillation is performed at a temperature sufficiently low to avoid precipitation of palladium.

25. A process according to claim 24, wherein the distillation is performed at a temperature which is lower than or equal to 110° C.

26. A process according to claim 24, wherein the distillation is performed at a temperature which is lower than or equal to 105° C.

27. A process according to claim 23, wherein the distillation is conducted at atmospheric pressure or at a pressure which is lower than atmospheric pressure.

28. A process according to claim 23, wherein the residue obtained after distillation, comprising the palladium, is acidified with an aqueous solution of hydrochloric acid.

29. A process according to claim 28, wherein the aqueous solution of hydrochloric acid employed comprises from 5% to 40% by weight of hydrochloric acid per weight of distillation residue.

30. A process according to claim 28, wherein the palladium is isolated from a mixture originating from the hydroxycarbonylation of butadiene to pentenoic acids and is recycled into a new butadiene hydroxycarbonylation.

31. A process according to claim 30, wherein the palladium is recycled after distillation of excess hydrochloric acid.

32. A process according to claim 29, wherein the palladium is isolated from a mixture originating from the hydroxycarbonylation of butadiene to pentenoic acids and is recycled into a new butadiene hydroxycarbonylation.

33. A process according to claim 32, wherein the palladium is recycled after distillation of excess hydrochloric acid.

* * * * *